(12) United States Patent
Day (10) Patent No.: US 11,786,902 B2
(45) Date of Patent: Oct. 17, 2023

(54) TUBES

(71) Applicant: 4titude Ltd, Wotton (GB)

(72) Inventor: Paul Francis Day, Dorking (GB)

(73) Assignee: 4titude Ltd, Wotton (GB)

( * ) Notice: Subject to any disclaimer, the term of this patent is extended or adjusted under 35 U.S.C. 154(b) by 2 days.

(21) Appl. No.: 17/647,440

(22) Filed: Jan. 7, 2022

(65) Prior Publication Data

US 2022/0339624 A1 Oct. 27, 2022

Related U.S. Application Data (63) Continuation of application No. 16/189,170, filed on Nov. 13, 2018, now abandoned.

(30) Foreign Application Priority Data

Nov. 10, 2017 (GB) ...................... 1718615

(51) Int. Cl.
| | | |
|---|---|---|
| *B01L 3/00* | (2006.01) | |
| *C12M 1/00* | (2006.01) | |
| *B01L 9/00* | (2006.01) | |
| *B29C 33/00* | (2006.01) | |
| *B29L 31/00* | (2006.01) | |

(52) U.S. Cl.
CPC ......... *B01L 3/5085* (2013.01); *B01L 3/50851* (2013.01); *B01L 3/50855* (2013.01); *B01L 3/5453* (2013.01); *C12M 23/22* (2013.01); *B01L 9/523* (2013.01); *B01L 2300/021* (2013.01); *B01L 2300/0829* (2013.01); *B01L 2300/0851* (2013.01); *B01L 2300/168* (2013.01); *B29C 33/0022* (2013.01); *B29L 2031/756* (2013.01)

(58) Field of Classification Search
CPC ............... B01L 3/5085; B01L 3/50851; B01L 3/50855; B01L 3/5453; B01L 9/523; B01L 2300/0829; B01L 2300/0851; B01L 2300/168; B29C 33/0022; B29L 2031/756
USPC ....................................... 435/288.4
See application file for complete search history.

(56) References Cited

U.S. PATENT DOCUMENTS

| | | |
|---|---|---|
| 5,002,889 A | 3/1991 | Klein |
| 5,180,555 A | 1/1993 | Monget |
| 5,670,118 A | 9/1997 | Sponholtz |
| 6,270,728 B1 | 8/2001 | Wijnschenk et al. |

(Continued)

FOREIGN PATENT DOCUMENTS

| | | |
|---|---|---|
| CN | 103240135 A | 8/2013 |
| EP | 2289625 | 2/2011 |

(Continued)

OTHER PUBLICATIONS

4titude Random Access Consumablesand Seals PDF (p. 2): https://www.brookslifesciences.com/sites/default/files/resources/brochures/4ti-FL-0014_Flyer_RAConsumables_201701_www.pdf(Year: 2017).

(Continued)

*Primary Examiner* — Michael L Hobbs
*Assistant Examiner* — Lenora A Abel
(74) *Attorney, Agent, or Firm* — Hamilton, Brook, Smith & Reynolds, P.C.

(57) ABSTRACT

A thin-walled microplate suitable for use in the Polymerase Chain Reaction (PCR) technique comprising a plurality of thin-walled tubes or wells arranged in a fixed array, each well having an upper portion with an open top and a lower, frustoconical portion having a substantially flat bottom.

26 Claims, 4 Drawing Sheets

(56) References Cited

U.S. PATENT DOCUMENTS

| | | | |
|---|---|---|---|
| 6,340,589 B1 | 1/2002 | Turner et al. | |
| 6,372,293 B1 | 4/2002 | Mathus et al. | |
| 7,347,977 B2 | 3/2008 | Guelzow et al. | |
| 2002/0098126 A1 | 7/2002 | Day | |
| 2010/0248213 A1 | 9/2010 | Feiglin | |
| 2014/0206079 A1 | 7/2014 | Malinoski et al. | |
| 2018/0369820 A1 | 12/2018 | Kaneko | |
| 2019/0247849 A1 | 8/2019 | Ueyama | |

FOREIGN PATENT DOCUMENTS

| | | |
|---|---|---|
| GB | 2568279 | 5/2019 |
| JP | 2003083984 | 3/2003 |
| JP | 2004053566 A | 2/2004 |
| JP | 2004191188 | 7/2004 |
| WO | 2014143044 A1 | 9/2014 |
| WO | 2017169196 A1 | 10/2017 |
| WO | 2019092390 | 5/2019 |

OTHER PUBLICATIONS

Thermo Scientific Matrix Data Sheet (2008): https://assets.thermofisher.com/TFS-Assets/LSG/Application-Notes/D 17414.pdf (See attached file, pp. 7 and 8). (Year: 2008).

PCT International Search Report and Written Opinion for International Application No. PCT/GB2018/000144 entitled "Thin Walled Microplate," dated Mar. 6, 2019, consisting of 10 pages.

International Preliminary Report on Patentability for Int'l Application No. PCT/GB2018/000144, Titled: Thin Walled Microplate, dated May 12, 2020.

Combined Search and Examination Report for GB Application No. GB 1718615.5, Titled: Low Profile Optical Window PCR Tubes, dated May 11, 2018.

4titude Random Access 96 Well Skirted Flat Bottom PCR Plate, 2D Coded, New Product Release, 8 pages, Jul. 2018.

REMP Consumables & Devices—Product Catalogue, Brooks Automation, 2014, 12 pages (redacted).

Section F-F

Detail F
FIG. 3G

FIG. 3H

TUBES

CROSS REFERENCE TO RELATED APPLICATIONS

This application is a continuation of U.S. application No. 16/189,170, filed Nov. 13, 2018, which claims priority under 35 U.S.C. § 119 or 365 to Great Britain Application No. GB1718615.6, filed on Nov. 10, 2017. The entire teachings of the above applications are incorporated herein by reference.

FIELD OF THE INVENTION

The present invention relates to thin-walled microplates for use in Polymerase Chain Reaction (PCR) reactions, comprising an array of thin-walled tubes or wells adapted for use in a thermal cycler. It is particularly applicable to an array of thin-walled tubes having open tops and lower, frustoconical portions having a substantially flat bottom.

BACKGROUND

A typical human cell consists of about 6 billion base pairs of DNA and 600 million bases of mRNA. Usually a mix containing millions of cells is used in sequencing the DNA or RNA using traditional methods. However by using Next Generation Sequencing (NGS) of DNA and RNA from a single cell, cellular functions can be investigated. In order to carry out experiments on a single cell the following steps are required: isolation of a single cell, nucleic acid extraction and amplification, sequencing library preparation, sequencing and bioinformatic data analysis. Needless to say, it is much more challenging to perform single cell sequencing in comparison with sequencing from cells in bulk. The minimal amount of starting materials from a single cell means that degradation, sample loss and/or contamination can cause pronounced effects on the quality of sequencing data. Nonetheless, recent technical improvements make single cell sequencing a promising tool for approaching otherwise intractable problems.

There is currently no standardized technique for single-cell isolation. Individual cells can be collected by micromanipulation, for example by serial dilution or by using a patch pipette or nanotube to harvest a single cell. Currently this separation step is generally carried out in sample tubes in which the cell(s) can be viewed, but which are inherently unsuitable for use in a PCR thermal cycler. Only once the operator has determined that only the desired single cell is present is this then transferred to a PCR tube or well for PCR and sequencing. This is because known PCR wells are not suitable for harvesting and viewing a single cell. This transfer from the harvesting tube to a PCR well requires an additional manipulation and can easily give rise to the problems of degradation, sample loss and/or contamination referred to above.

A further problem with current PCR wells is how to apply a marking to a PCR well to give it a unique identity. A cap to the PCR tube can be labelled, but caps can become detached, and this is not the same as labelling the tube itself. The upper part of the outside of a PCR well can be labelled but this involves producing a label on a tightly curved surface, making the machine reading of any label problematic. Such machine reading becomes impossible if the PCR well in question is in the middle of an array of wells, for example a 12 by 8 array of 96 tubes or wells.

It is an object of the present invention to overcome or mitigate some or all of the disadvantages outlined above.

SUMMARY OF THE INVENTION

According to a first aspect of the present invention there is provided a thin-walled microplate according to Claim 1. For example, there is described a thin-walled microplate suitable for use in the Polymerase Chain Reaction (PCR) technique comprising a plurality of thin-walled tubes or wells arranged in a fixed or random access array, each well having an upper portion with an open top and a lower, frustoconical portion having a substantially flat bottom. By providing a flat bottomed well in an array of wells suitable for use in the PCR technique a wide variety of new possibilities are created. It will be understood that the bottom to the well will have an internal surface, inside the well, and an external surface on the outside of the well. The bottom surface of the well can be made substantially planar, and horizontal when stood on a horizontal surface, such that a single cell in the tube can be viewed through the top of the tube. If the flat bottom surface of the well is made substantially transparent, i.e. incorporates an optically clear window, then a single cell, or some other feature such as fluorescence within the well, can be viewed from below the well through this optically window, as well as from above. Or alternatively the bottom surface, preferably the external bottom surface, may carry some form of label, preferably in the form of a unique machine readable code.

Preferably the bottom surface of each of the wells in the array are in substantially the same horizontal plane such that items such as a cell or cells in the bottom of different wells in the array are in substantially the same focal plane when viewed from above through the opening in the top of the respective wells, or from below in the case of a well with a substantially transparent flat bottom window. By 'in substantially the same plane' is meant that the distance to the bottom of each well is the same to within +/− 0.1 mm, and more preferably within +/− 0.05 mm or better.

Preferably the external diameter of the flat bottom surface or portion of each well is in the range 2.0 mm to 4.5 mm, more preferably in the range 2.5 mm to 3.5 mm, with a particularly preferred diameter being 3 mm.

Preferably the substantially flat bottom surface of one or more wells in a random access array includes a machine readable code, and more preferably substantially all the wells in the randomly accessible array carry such a code.

Preferably the machine readable code is readable using an optical vision system, sometimes referred to as a Machine Vision (MV) System.

Preferably the machine readable code is on the external surface of the substantially flat bottom surface of the well.

In a particularly preferred embodiment the flat bottom surface or window of each well incorporates a protection ring or bead, and preferably the protection ring/bead is located substantially on the outer bottom peripheral circumference of the flat bottom surface or window. This bead, ring or downstand serves to protect the flat bottom surface of the well from accidental damage caused by, for example, solvents or abrasion. Contact with solvents for example might degrade any code or other label on the bottom of the well. Any abrasion would detract from optical measurements made through an otherwise substantially optically transparent window, or interfere with the 2D code reading. Keeping the flat bottom exterior surface of the well distanced away from potential contaminants is an important feature of the invention.

Preferably the substantially flat bottom surface of each well is formed from substantially clear material, such that each well has an optically-clear window. This feature, if present, provides the advantages set out above.

Preferably the array of thin-walled tubes or wells are held in a substantially rigid frame, and this frame may be formed from a different plastics materials to the wells, such that the substantially rigid frame is formed from a first plastics material and the tubes or wells are formed from a second plastics material that is suitable for PCR use. The wells may be permanently fixed in the frame or may be individually removable from the frame and therefore randomly accessible.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Preferred embodiments of the present invention will now be described by way of example only with reference to the accompanying Figures wherein.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

FIG. 3 illustrates various views of one embodiment of a thin-walled microplate according to the present invention, in this example a microplate containing a 12×8 array of 96 wells. A 12×8 array is given here by way of example only, and other arrays having different configurations and numbers of wells are possible. FIGS. 1A to 1D show various views of one of the individual thin-walled wells used in the array of wells shown in FIG. 3. The thin-walled reaction wells shown in more detail in FIG. 1 are designed specifically for use in performing Polymerase Chain Reaction (PCR) experiments in a thermal cycler. Each well comprises a hollow tube 10 having an opening 11 at a first end, a short substantially straight sided upper section 18 adjacent to the open end, and a frustoconical section 12 which is closed in a fluid-tight fashion by a substantially flat bottom portion 13, having internal and external bottom surfaces. The wells are formed from a plastics material with good heat transfer properties and which is suitable for PCR, such as polypropylene.

It is important that the bottom of each well is substantially flat and substantially horizontal when the microplate is positioned on a horizontal surface. It is also important that the inner bottom surface of each well in an array is substantially equidistant from the top of the microplate. By substantially equidistance it is meant that the distance to the bottom of each well is the same within +/− 0.1 mm, and preferably +/−0.05 mm or better. This tolerance arrangement means that an operator can view an item, such as a single cell, resting on the flat bottom surface of any of the wells through an optical imaging system, without having to alter the focal plane of the instrument. This significantly speeds up the process of checking the content of each well.

Figure 1A:
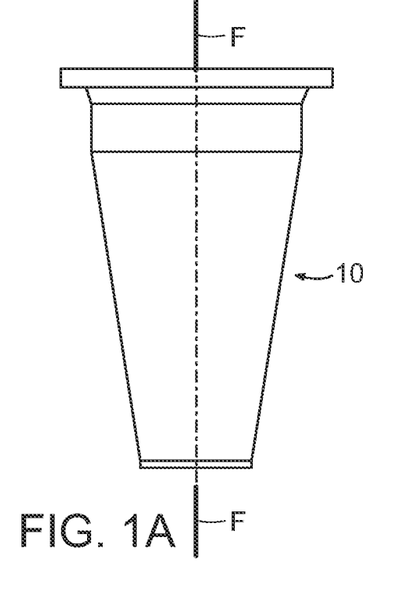
FIGS. 1A to 1D show side elevation, cross-sectional, bottom elevation and perspective views respectively of a single thin-walled PCR well.
Figure 1B:
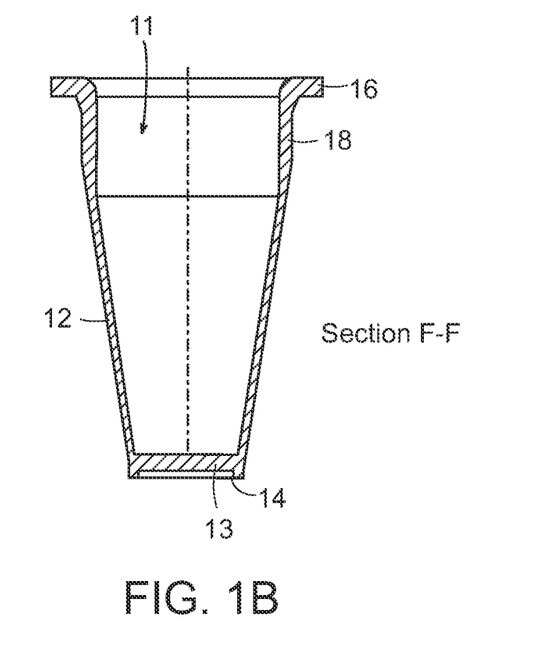
Figure 1C:
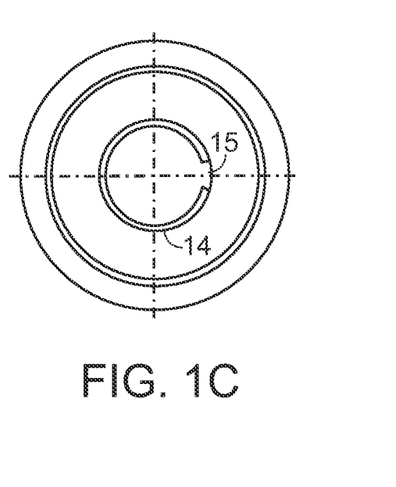

The flat bottom surface may advantageously be made substantially optically clear or transparent, thus creating a substantially clear optical window in the bottom of the well. One method of achieving this high transparency is to highly polish the opposing surfaces of the moulding tool that form the bottom of each well. In this way visual observations may also be made from underneath the microplate as well as from above. Observation of other effects such as colour changes or fluorescence from the contents of a well may also be made from above or below the microplate. This is the first time this has been possible in an array of PCR wells in a microplate.

Figure 2:
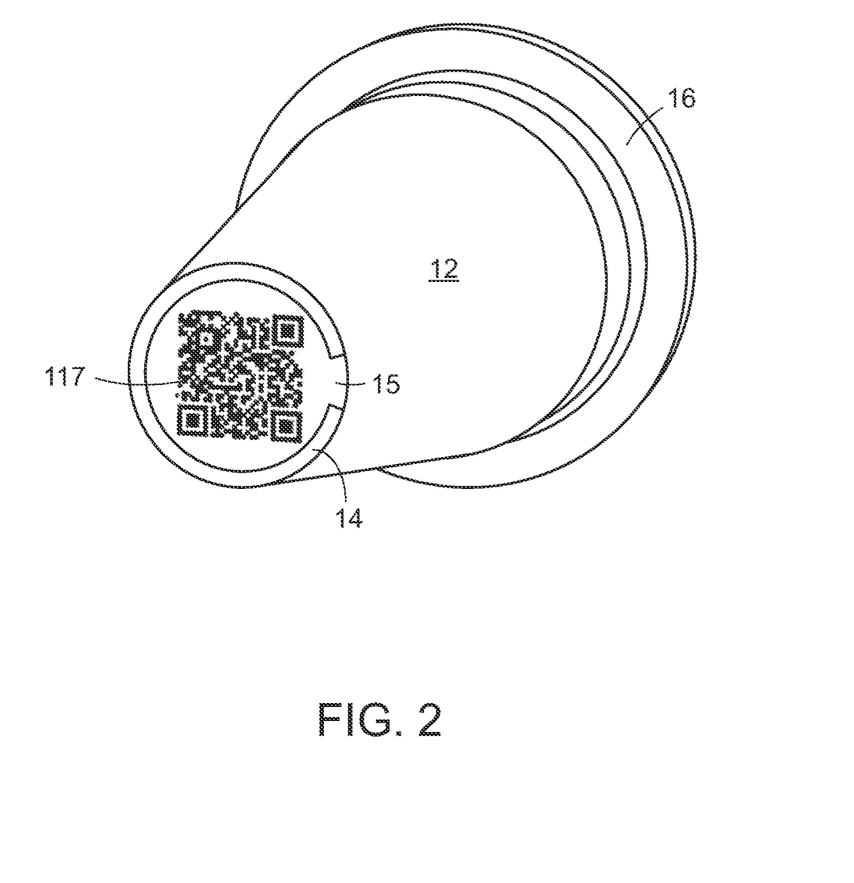
FIG. 2 shows a perspective view of a single thin-walled PCR well as shown in FIG. 1 with a 2D machine readable code on the bottom of the well.
Figure 3A:
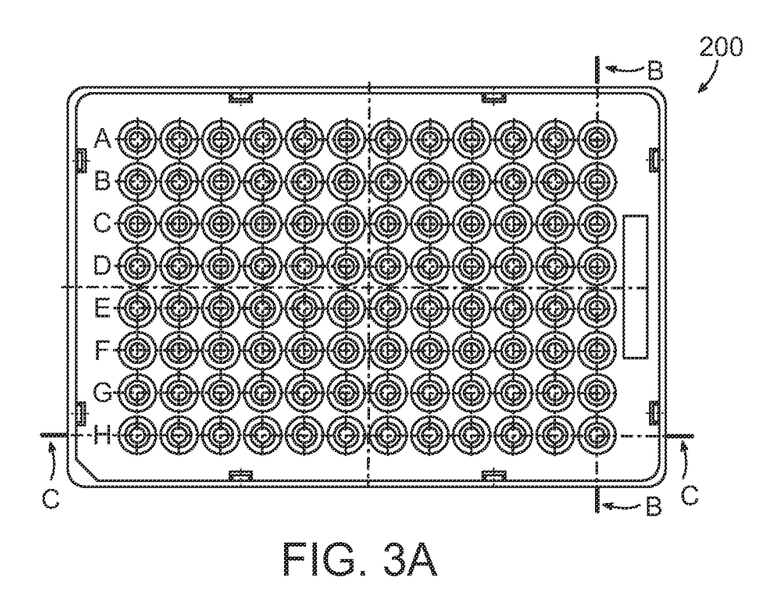
FIG. 3A to 3H show top elevation, side cross-section along C-C, side cross-section along B-B, an end elevation, a side elevation, a partial view from underneath, detail F from FIG. 3B, and a perspective view from above to one side of a 96 well random access array of the type of wells shown in FIG. 1 in a frame.
Figure 3B:
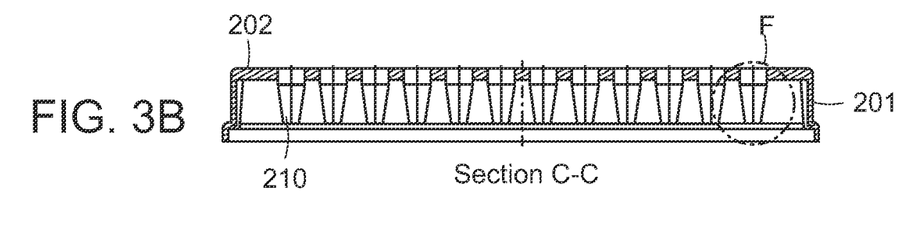
Figure 3C:
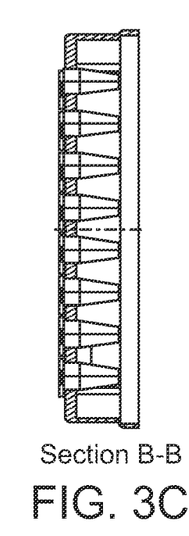
Figure 3D:
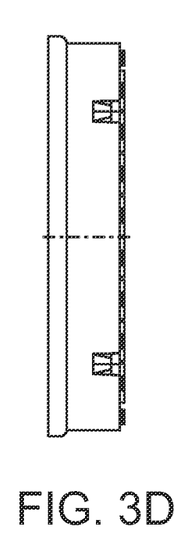
Figure 3E:
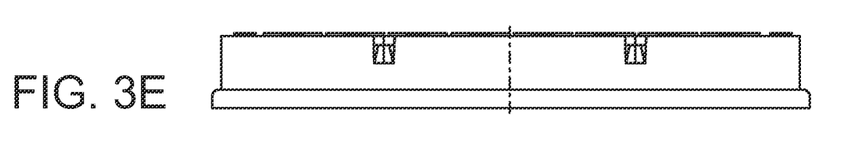
Figure 3F:
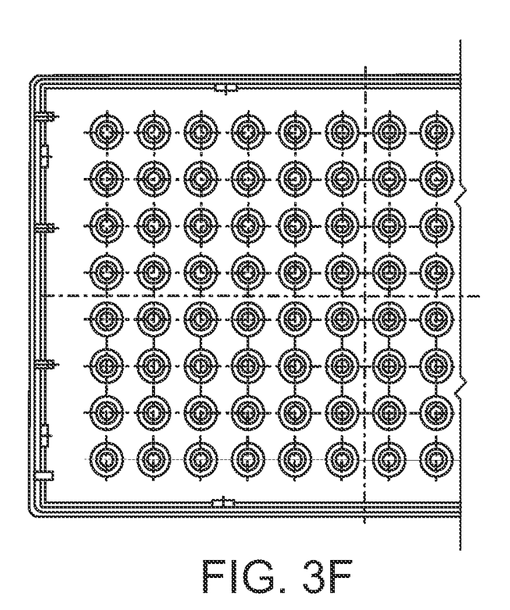
Figure 3G:
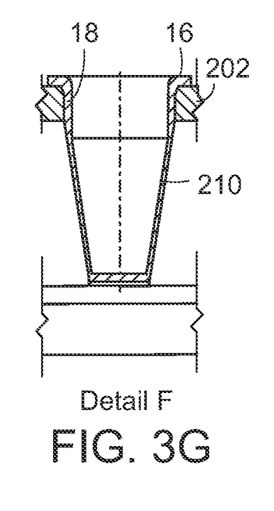
Figure 3H:
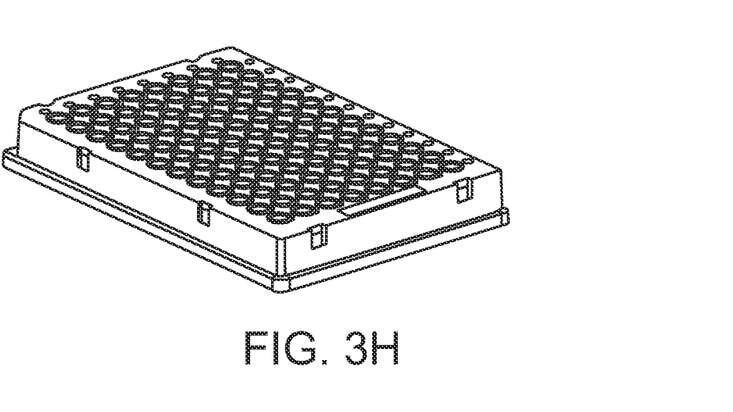

In a further embodiment, rather than having an optically clear window on the bottom of a well, the flat-bottom surface or portion can carry some form of label or machine readable code. One example of this is shown in FIG. 2 which shows a 2D code 117 on the bottom of a well. There are a wide variety of known ways to apply machine readable data to the bottom of a test tube, but not a PCR well. For example, U.S. Pat. No. 6,372,293B (Matrix Technologies Corp) describes a method of applying a multi-layer coating onto a planar exterior surface of a test tube and removing portions of the outer layer. U.S. Pat. No. 6,270,728B (Micronic B.V)

describes a process of laser burning a code onto the base of a test tube. A further method is to use a treatment, for example a corona treatment, to change the properties of the exterior of the flat-bottom surface of each well. A machine readable code can then be applied directly onto the bottom of each treated well. This is a particularly cost effective method of applying a code to the bottom of each well.

The provision of PCR tubes with unique machine readable codes represents a real advance for experimenters, particularly when those tubes are in a random access array as illustrated in FIG. 3. In this example the individual tubes 210 are not integrally (permanently) fixed in the rigid frame 201, 202 but can be individually removed from the frame and are therefore randomly accessible. That is to say, an operator can push any one tube upwards out of the frame in order to process that particular tube without disturbing the other 95 tubes that are still held captive in the frame.

It will be appreciated that in an alternative embodiment the tubes may be integrally (permanently) fixed into a rigid frame, if that is the format preferred by the experimenter. Methods of making integrally (permanently) fixed arrays of wells are known, such as those described in U.S. Pat. No. 6,340,589B1 (Eppendorf).

Figure 1D:
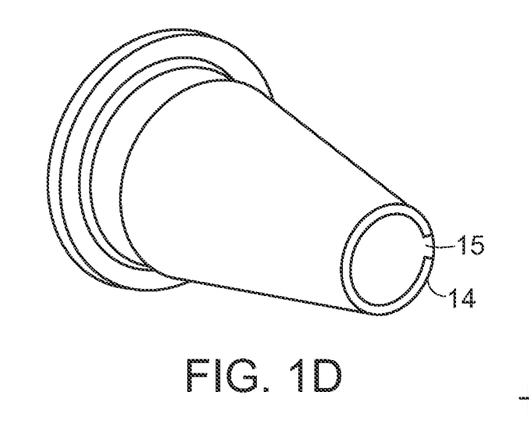

Whether the outer surface of the bottom of each well is optically clear or carries a machine readable code, it is important that the surface is protected in some way. One method of giving a degree of protection is to incorporate a protection ring or bead 14, around part of or around the entire outer circumference of the bottom surface, as shown in FIGS. 1B, 1D and 2. This protection ring can be formed as a downstand around some of or substantially the entire outer perimeter of the bottom of the well in the moulding process.

The protection ring need not be present around the entire circumference of the bottom of the well, and may include one or more gaps 15 as shown in FIGS. 1D and 2. Furthermore, it need not take the form of a conventional 'ring', but instead could take the form of a plurality of individual protrusions set around the perimeter of the bottom portion. The protection ring, or its equivalent, serves to keep the outer surface of the flat-bottom away from any surface that it might otherwise rest on. This keeps contaminants, such as solvents, away from the machine readable code and also prevents the surface from getting scratched or abraded. Such abrasion would impair the quality of imaging if the bottom of the well is optically clear, as well as potentially destroy the integrity and readability of any code.

The diameter of the bottom surface of the frustoconical portion of the wells is an important feature of this invention. The diameter, which is measured to the inside edge of any protection ring, is preferable 2.0 to 4.5 mm and more preferable 2.5 to 3.5 mm. A particularly preferred diameter for the window in the bottom surface is 3 mm ±10%.

By way of example only of some other typical dimensions, the wall thickness of the side wall of each well in the frustoconical portion is 0.25 mm ±0.025 mm, which is a typical wall thickness for carrying out PCR reactions. The thickness of the bottom portion or surface is not critical, as it is not in direct contact with the thermal cycler, and a typical thickness for the bottom of the well is 0.5 mm. The angle of the side wall of each well in the frustoconical section must correspond to the well angle found in commercially available thermal cyclers. Typically, this angle is 17 degrees. The full well volume of a typical well is in the region of 200 microlitres. The top of each well could incorporate a raised rim or chimney if desired (not shown), to facilitate sealing the wells with some form of sealing strip or film, but this is not essential.

As referred to above, FIG. 3 illustrates a thin-walled microplate 200 of the invention, containing a 12 by 8 array of 96 wells of the type illustrated in FIG. 1 or FIG. 2. As explained above, the individual wells 210 are either fixed or removably held captive in a substantially rigid frame made up of a skirt portion 201 and a deck portion 202. In the example illustrated in FIG. 3, the wells are held in a randomly accessible fashion in the deck portion by a collar 16 and a substantially planar region 18 close to the top of each well. The substantially planar portion of each well may incorporate a slight indentation in order that the wells are held more tightly in the substantially rigid frame, and are therefore less prone to being dislodged accidently during handling. The rigid frame can be made of a first plastics material such as a polycarbonate, a nylon or Acrylonitrile Butadiene Styrene (ABS), and the wells formed from a second plastics material that is suitable for PCR such as polypropylene. It will be understood that new materials do become available over time and the optimum materials for both components will be selected by a materials expert as required.

In summary, in a first version of the present invention there is provided an array of tubes with highly polished flat optical bases, or optical windows, where the wells are substantially permanently fixed in a rigid frame in, for example, a 12×8 array of 96 wells. This arrangement is of interest to scientists who want to make optical measurements of a tube's contents from either above or below the plate, i.e. by using a laboratory plate reader as a pre-screen in applications like single cell PCR procedures.

There is a growing trend in the market for scientists to want to do single cell PCR whereby they populate a screening plate that is not a PCR plate but in which each individual tube in the plate has an optical base and then after correct identification of the desired target cell transfer that cell to a PCR well for lysis and amplification. A plate with an array of PCR wells with flat optical windows in the bottom of each well enables scientists for the first time to screen a plate for single cell morphology and to confirm there is only one cell per well and then use the same plate for performing the PCR. This offers a huge advantage in that the scientist does not have to capture and transfer a single cell from one plate or well to another, with the inherent possibility of degradation, sample loss and/or contamination.

In a second version, wells incorporating optical windows in the 12×8 array of wells are not integrally (permanently) fixed in the rigid frame but can be individually removed from the frame and are therefore randomly accessible. That is to say, an operator can push any one tube out of the frame to process that particular tube without disturbing the other 95 tubes that are still held captive in the frame.

In a third version of the present invention, a flat bottom PCR tube we can be used to carry a 2D code on the flat bottom surface. This 2D coded PCR tube can then be tracked through the laboratory work flow, which is becoming an important feature for DNA storage and for the Molecular Diagnostic market. Thus, flat bottomed PCR tubes with a modified treated bottom surface that has been labelled with a 2D code are held in a randomly accessible array in a substantially rigid frame, such as a 12×8 array of labelled tubes, where the tubes are not integrally (permanently) fixed in the rigid frame but can be individually removed from the frame and are therefore randomly accessible. The key point to labelling all 96 tubes on the underside of the flat bottom surface is that these tubes can be randomly accessed and removed from the array with their code intact. These random accessible 96 tubes may be processed in a 96 well format but can then be accessed individually in downstream processing procedures/experiments. The flat bottom PCR tube with machine readable code on the flat bottom surface can have the code positioned on the flat bottom surface in such a way as to still allow the flat bottom to serve as a flat optical window for readings.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A thin-walled microplate for use in a Polymerase Chain Reaction PCR technique comprising a plurality of wells arranged in an access array in a rigid frame, each well having a short upper portion with an open top, a longer, lower, frustoconical portion of thickness of about 0.25 mm, and a flat bottom, the sidewall of the frustoconical portion being of material and thickness having heat transfer properties suitable for PCR, and the flat bottom of each of the wells in the array having a diameter of an external flat bottom surface in the range of 2.0 mm to 4.5 mm and an internal flat bottom surface that extends on a horizontal plane such that the internal flat bottom surface of each well is equidistant from the top of the microplate, wherein the wells are not integrally fixed in the rigid frame but can be individually removed from the frame and are therefore randomly accessible, and wherein the flat bottom surface of each well in the array incorporates a 2-D machine-readable code that is readable using an optical vision system.

2. The thin-walled microplate according to claim 1 further comprising a protection ring or bead that extends axially down from the external flat bottom surface to protect the external flat bottom surface.

3. The thin-walled microplate according to claim 2, wherein the protection ring or bead is located on an outer circumference of the substantially flat bottom and the diameter of the external flat bottom surface is measured to the inside edge of the ring or bead.

4. The thin-walled microplate according to claim 1 wherein the each well is sized and shaped to correspond to the size and shape of available thermal cyclers, including the lower, frustoconical portion being angled at about 17 degrees.

5. The thin-walled microplate according to claim 1 wherein the each well is sized and shaped to correspond to the size and shape of available thermal cyclers, including the lower, frustoconical portion being angled at about 17 degrees, each well further comprising a protection ring or bead that extends axially down from the external flat bottom surface to protect the external flat bottom surface, the protection ring or bead being located substantially on an outer circumference of the flat bottom. and the diameter of the external flat bottom surface is measured to the inside edge of the ring or bead.

6. The thin-walled microplate according to claim 1, wherein the diameter of the external flat bottom surface is in the range of 2.5 mm to 3.5 mm.

7. The thin-walled microplate according to claim 1 wherein the thickness of the frustoconical portion is 0.25 mm. +/− 0.025 mm.

8. The thin-walled microplate according to claim 1, wherein the machine-readable code is on the external surface of the flat bottom.

9. The thin-walled microplate according to claim 1 configured such that a single cell in the tube can be viewed through the top of the well.

10. The thin-walled microplate according to claim 1, wherein a distance from the open top to the inner bottom surface of each well is the same to within +/− 0.1 mm.

11. The thin-walled microplate according to claim 1, wherein a distance from the open top to the inner bottom surface of each well is the same to within +/− 0.05 mm.

12. The thin-walled microplate according to claim 1, wherein the wells are held tightly in the rigid frame.

13. The thin-walled microplate according to claim 1 wherein each well comprise an indentation in the short upper portion to hold the well in the rigid frame.

14. A well for placement in an array within a rigid frame for use in a Polymerase Chain Reaction PCR technique comprising: a short upper portion with an open top; a longer, lower, frustoconical portion of thickness of about 0.25 mm; and a flat bottom; the sidewall of the frustoconical portion being of material and thickness having heat transfer properties suitable for PCR; the flat bottom of the well having a diameter of an external flat bottom surface in the range of 2.0 mm to 4.5 mm and an internal flat bottom surface that extends on a horizontal plane such that the internal flat bottom surface of each well is equidistant from the top of the microplate; the well is configured to be individually removed from the frame and is therefore randomly accessible; and the flat bottom surface of the well incorporates a 2-D machine-readable code that is readable using an optical vision system.

15. The well according to claim 14 further comprising a protection ring or bead that extends axially down from the external flat bottom surface to protect the external flat bottom surface.

16. The well according to claim 15, wherein the protection ring or bead is located substantially on an outer circumference of the flat bottom and the diameter of the external flat bottom surface is measured to the inside edge of the ring or bead.

17. The well according to claim 14 wherein the well is sized and shaped to correspond to the size and shape of available thermal cyclers, including the lower, frustoconical portion being angled at about 17 degrees.

18. The well according to claim 14 wherein the well is sized and shaped to correspond to the size and shape of available thermal cyclers, including the lower, frustoconical portion being angled at about 17 degrees, the well further comprising a protection ring or bead that extends axially down from the external flat bottom surface to protect the external flat bottom surface, the protection ring or bead being located on an outer circumference of the substantially flat bottom and the diameter of the external flat bottom surface is measured to the inside edge of the ring or bead.

19. The well according to claim 14, wherein the diameter of the external flat bottom surface is in the range of 2.5 mm to 3.5 mm.

20. The well according to claim 14 wherein the thickness of the frustoconical portion is 0.25 mm. +/− 0.025 mm.

21. The well according to claim 14, wherein the machine-readable code is on the external surface of the flat bottom.

22. The well according to claim 14 configured such that a single cell in the tube can be viewed through the top of the well.

23. The well according to claim 14, wherein a distance from the open top to the inner bottom surface of the well is the same to within +/− 0.1 mm.

24. The well according to claim 14, wherein a distance from the open top to the inner bottom surface of each well is the same to within +/− 0.05 mm.

25. The well according to claim 14 wherein the well is configured to be held tightly in the rigid frame.

26. The well according to claim 14 wherein the well comprises an indentation in the short upper portion to hold the well in the rigid frame.

* * * * *